United States Patent
Fialkov

(10) Patent No.: US 10,966,688 B2
(45) Date of Patent: Apr. 6, 2021

(54) IMAGE REGISTRATION FOR CT OR MR IMAGERY AND ULTRASOUND IMAGERY USING MOBILE DEVICE

(71) Applicant: Rational Surgical Solutions, LLC, Des Moines, IA (US)

(72) Inventor: Jonathan Fialkov, Des Moines, IA (US)

(73) Assignee: Rational Surgical Solutions, LLC, Des Moines, IA (US)

( * ) Notice: Subject to any disclaimer, the term of this patent is extended or adjusted under 35 U.S.C. 154(b) by 741 days.

(21) Appl. No.: 14/658,436

(22) Filed: Mar. 16, 2015

(65) Prior Publication Data

US 2016/0058424 A1  Mar. 3, 2016

Related U.S. Application Data

(60) Provisional application No. 62/041,721, filed on Aug. 26, 2014.

(51) Int. Cl.
*A61B 8/08* (2006.01)
*A61B 5/055* (2006.01)
(Continued)

(52) U.S. Cl.
CPC ........... *A61B 8/5261* (2013.01); *A61B 5/055* (2013.01); *A61B 6/4405* (2013.01);
(Continued)

(58) Field of Classification Search
CPC . G06T 2200/24; G06T 3/0068; A61B 8/5261; A61B 5/055; A61B 6/4405;
(Continued)

(56) References Cited

U.S. PATENT DOCUMENTS 7,623,697 B1 * 11/2009 Hughes ............... G06F 3/04845
345/626
8,160,314 B2 * 4/2012 Ramamurthy ........... G06T 5/50
382/128
(Continued)

FOREIGN PATENT DOCUMENTS

| WO | 2006092594 | | 9/2006 |
| WO | 2014031531 | A1 | 2/2014 |
| WO | 2014096993 | A1 | 7/2014 |

OTHER PUBLICATIONS

United States Patent and Trademark Office, "International Search Report and written opinion", issued in connection to PCT/US15/46728, dated Nov. 30, 2015, 8 pages.
(Continued)

*Primary Examiner* — Katherine L Fernandez
*Assistant Examiner* — Colin T. Sakamoto
(74) *Attorney, Agent, or Firm* — McKee, Voorhees & Sease, PLC

(57) ABSTRACT

A method for fusion of live ultrasound imagery with computed tomography (CT) scan images or magnetic resonance images, the method comprising steps of acquiring a series of CT scan images or magnetic resonance images, acquiring a series of ultrasound images, applying a manual registration process on a computing device to register each of the CT scan images or magnetic resonance images with corresponding ultrasound images, and displaying on a display associated with the computing device the live ultrasound imagery and corresponding CT scan images or magnetic resonance images.

29 Claims, 11 Drawing Sheets

(51) Int. Cl.
  *A61B 6/03* (2006.01)
  *A61B 8/00* (2006.01)
  *A61B 10/02* (2006.01)
  *A61B 6/00* (2006.01)
  *G06T 3/00* (2006.01)
  *A61B 90/00* (2016.01)
  *A61B 18/00* (2006.01)

(52) U.S. Cl.
  CPC .......... *A61B 6/5247* (2013.01); *A61B 8/4416* (2013.01); *A61B 8/4427* (2013.01); *A61B 8/462* (2013.01); *A61B 8/463* (2013.01); *A61B 8/466* (2013.01); *A61B 8/468* (2013.01); *A61B 8/469* (2013.01); *A61B 10/02* (2013.01); *A61B 90/37* (2016.02); *G06T 3/0068* (2013.01); *A61B 6/032* (2013.01); *A61B 18/00* (2013.01); *A61B 2018/00333* (2013.01); *A61B 2018/00529* (2013.01); *A61B 2018/00535* (2013.01); *A61B 2018/00577* (2013.01); *A61B 2090/365* (2016.02); *A61B 2090/374* (2016.02); *A61B 2090/378* (2016.02); *A61B 2090/3762* (2016.02); *A61B 2576/00* (2013.01)

(58) Field of Classification Search
  CPC ... A61B 6/5247; A61B 8/4416; A61B 5/7425; A61B 8/5238; A61B 8/5246; A61B 8/5253
  See application file for complete search history.

(56) References Cited

U.S. PATENT DOCUMENTS

| | | | | |
|---|---|---|---|---|
| 8,605,964 | B2* | 12/2013 | Fichtinger | A61B 8/13 382/128 |
| 2006/0020204 | A1* | 1/2006 | Serra | G06T 7/38 600/437 |
| 2006/0253024 | A1 | 11/2006 | Altmann et al. | |
| 2007/0167806 | A1* | 7/2007 | Wood | A61B 8/13 600/459 |
| 2007/0258626 | A1 | 11/2007 | Reiner | |
| 2009/0097723 | A1* | 4/2009 | Washburn | G06T 7/0012 382/128 |
| 2009/0129644 | A1* | 5/2009 | Daw | G06F 19/327 382/128 |
| 2011/0028843 | A1* | 2/2011 | Hyun | G06T 7/38 600/443 |
| 2011/0134113 | A1* | 6/2011 | Ma | A61B 8/4245 345/419 |
| 2012/0071753 | A1* | 3/2012 | Hunter | A61B 5/415 600/424 |
| 2012/0237102 | A1* | 9/2012 | Savitsky | G09B 23/286 382/131 |
| 2012/0262453 | A1* | 10/2012 | Endo | A61B 8/5246 345/419 |
| 2013/0231559 | A1* | 9/2013 | Hyun | A61B 5/0035 600/427 |
| 2014/0235997 | A1* | 8/2014 | Smith | A61B 17/3472 600/424 |
| 2014/0235998 | A1* | 8/2014 | Kim | A61B 8/5261 600/424 |
| 2015/0371361 | A1* | 12/2015 | Kim | G06T 3/0068 382/128 |
| 2017/0164931 | A1* | 6/2017 | Ng | A61B 8/0841 |

OTHER PUBLICATIONS

Amalou, Hayet et al., "Multimodality Fusion with MRI, CT, and Ultrasound Contrast for Ablation of Renal Cell Carcinoma" Case Report in Urology, vol. 2012, Article ID 390912, 5 pages.
Siemens, "eSieFusion Imaging Pioneering Technology", www.siemens.com/S3000, Siemens Medial Solutions USA Inc., CC1102 0213X, 2 pages, Feb. 2013.
Toshiba America Medical Systems, Inc., www.medical.toshiba.com, ULWP12062US, 2012, 4 pages.
Wang, Zhe et al., "Registration of Ultrasound Images Using an Information-Theoretic Feature Detector", New Jersey Institute of Technology and Siemens Corporate Research, 4 pages, Apr. 2007.
Wein, Wolfgang, Dissertation "Multimodal Integration of Medical Ultrasound for Treatment Planning and Interventions", 165 pages, Jun. 22, 2007.

* cited by examiner

IMAGE REGISTRATION FOR CT OR MR IMAGERY AND ULTRASOUND IMAGERY USING MOBILE DEVICE

CROSS-REFERENCE TO RELATED APPLICATIONS

This application claims priority under 35 U.S.C. § 119 to provisional application Ser. No. 62/041,721 filed Aug. 26, 2014, herein incorporated by reference in its entirety.

FIELD OF THE INVENTION

The present invention relates to medical imagery. More specifically, but not exclusively, the present invention relates to the fusion of computed tomography (CT) or magnetic resonance (MR) imagery and ultrasound imagery using a manual image registration process.

BACKGROUND OF THE ART

Computed tomography (CT) and magnetic resonance (MR) imagery are well known and widely used in medical applications. Ultrasound imagery is also well known and widely used. In certain applications these types of imagery may be used interventionally in minimally invasive procedures or intraoperatively as a part of the surgical process.

Ultrasound technology may be used to assist in various types of medical procedures including needle biopsies. The use of ultrasound technology allows for improvements relative to completely blind biopsies. However, imaging using other techniques such as CT and MR systems may be superior in certain situations such as by allowing for better depicting structure. Yet there are problems with using CT or MR systems.

For example, despite the availability of CT and MR systems, such systems typically have great costs and thus are less accessible than ultrasound systems. In addition, the use of CT and MR systems may involve greater discomfort to patients. Thus, there are various procedures where although CT and MR imagery could theoretically be used, ultrasound is preferred due to cost, availability, convenience, and safety.

There have been some attempts at fusion of imagery from CT or MR systems and ultrasound imagery. Yet such systems do not appear to be generally commercially available perhaps due to attendant complexities.

What is needed are improved methods and systems for use in image fusion.

SUMMARY OF THE INVENTION

Therefore, it is a primary object, feature, or advantage of the present invention to improve over the state of the art.

It is a further object, feature, or advantage of the present invention to provide for image fusion which allows for CT or MR imagery to be fused with ultrasound imagery.

It is a still further object, feature, or advantage of the present invention to improve the information available to a physician performing certain procedures such as needle biopsies or ablations.

Another object, feature, or advantage of the present invention is to provide a solution which may be software only using commercial off-the-shelf hardware.

Yet another object, feature, or advantage of the present invention is to provide a solution which is cost effective.

A still further object, feature, or advantage of the present invention is to provide a solution which is easy, convenient, and intuitive to use.

It is a further object, feature, or advantage of the present invention to provide for using data from a three-dimensional (3D) model constructed from CT or MR imagery to assist with fusion with ultrasound imagery.

One or more of these and/or other objects, features, or advantages of the present invention will become apparent from the specification and claims that follow. No single embodiment need meet or include every object, feature, or advantage. It is contemplated that different embodiments may have different objects, features, or advantages.

According to one aspect, a method for fusion of live ultrasound imagery with computed tomography (CT) scan images or magnetic resonance images is provided. The method includes steps of acquiring a series of CT scan images or magnetic resonance images and acquiring a series of ultrasound images. The method further includes applying a manual registration process on a computing device to register each of the CT scan images or magnetic resonance images with corresponding ultrasound images, and displaying on a display associated with the computing device the live ultrasound imagery and corresponding CT scan images or magnetic resonance images.

According to another aspect, a method for fusion of live ultrasound imagery with computed tomography (CT) scan images or magnetic resonance images for use on a tablet device is provided. The method includes downloading into the tablet device a series of CT scan images or magnetic resonance images, downloading into the tablet device a series of ultrasound images, displaying on a display of the tablet device a graphical user interface to a user for applying a manual registration process on the tablet device to register each of the CT scan images or magnetic resonance images with corresponding ultrasound images, receiving into the tablet device the live ultrasound imagery from an ultrasound system, and displaying on the display of the tablet device the live ultrasound imagery and corresponding CT scan images or magnetic resonance images.

DETAILED DESCRIPTION

The present invention provides for the fusion of CT or MR images and ultrasound images. Thus, biopsies, ablations or other procedures may be performed using an ultra sound device and benefiting from previously acquired CT or MR images. Moreover, according to one embodiment a physician uses a tablet device such as an Apple® iPad® to manually register ultrasound images to CT or MR images and may use such a device during a medical procedure. The manual registration process may be performed in a simple and intuitive manner.

Figure 1:
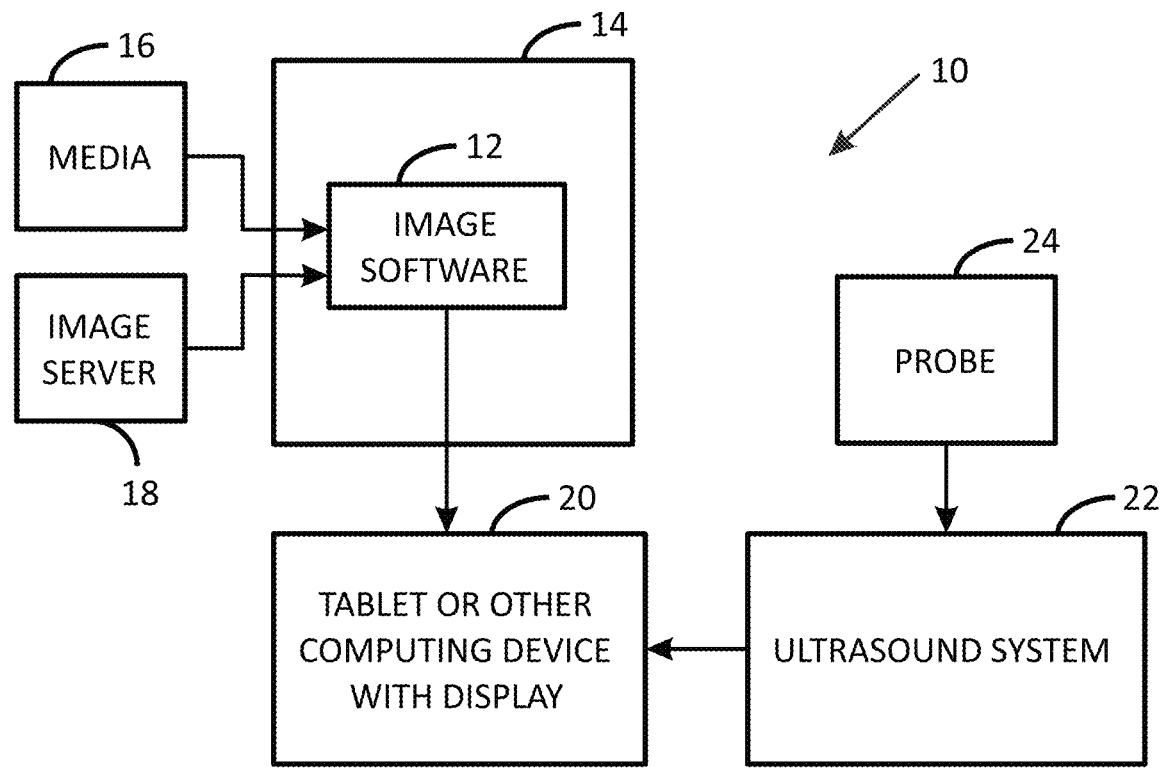
FIG. 1 illustrates one example of a system.

FIG. 1 illustrates one example of a system. As shown in FIG. 1, a system 10 includes image software 12 which may be executed on a computing device 14. The image software 12 may be used with images which are stored on media 14. The media 14 may be any type of non-transitory machine readable storage medium such as solid state memory, magnetic memory, optical memory or otherwise. The image software 12 may also be used with images which are accessed from an image server.

The image software may be an image processing application such as OsiriX or other application which may read imagery from medical equipment. One common format for such imagery is the DICOM format. In one embodiment, the image software 12 is executed on a computing device and then selected images may be communicated to a tablet 20 or other computing device. It is contemplated that image software 12 could also execute directly on the tablet 20. As will be explained in further detail later herein, imagery used for fusion purposes (such as CT or MR images) may be loaded onto the tablet 20. The tablet 20 may also be operatively connected to an ultrasound system. This may be a wired or wireless connection such as through a USB or network connection. In addition, the tablet may be mounted to the ultrasound system for convenience. The tablet is configured to display in real-time ultrasound imagery from the ultrasound system 22. The ultrasound system 22 includes a probe 24.

Figure 2:
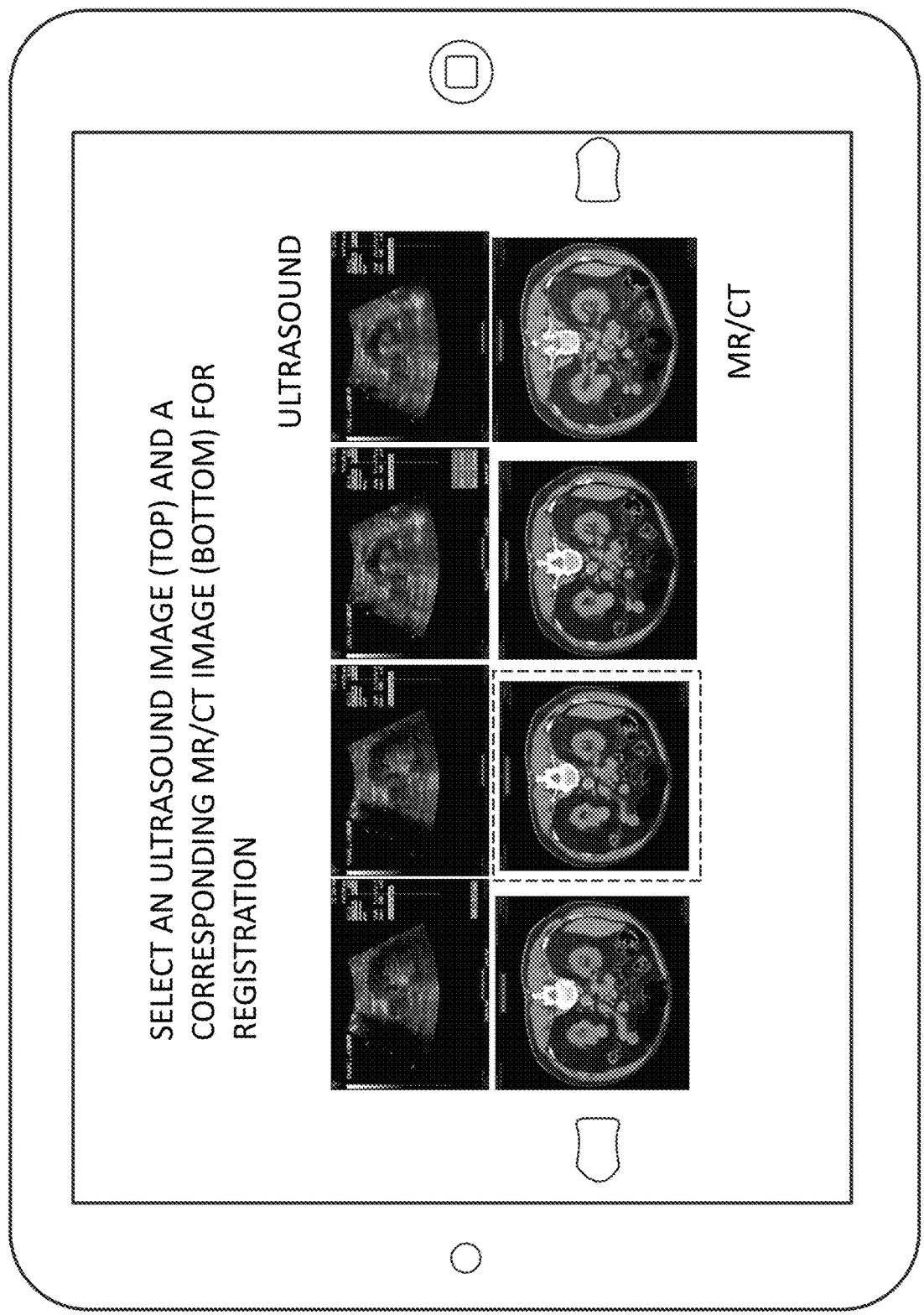
FIG. 2 illustrates selection of a CT scan image as a part of a manual image registration process.
Figure 3:
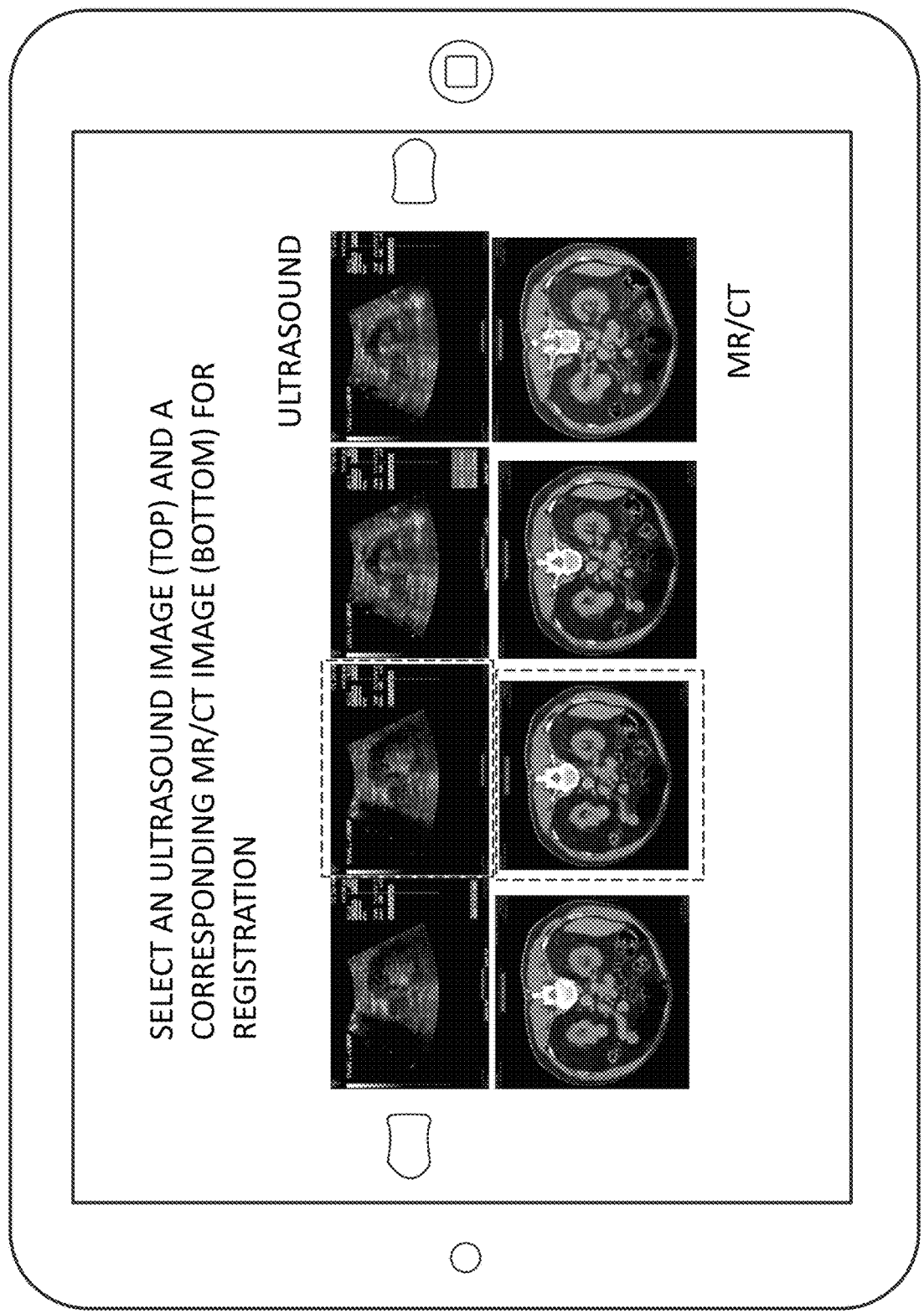
FIG. 3 illustrates selection of an ultrasound image corresponding to the selected CT scan image as a part of a manual image registration process.

In one example, CT scan images may be loaded onto the tablet device. In addition, ultrasound images may be acquired using the ultrasound system for image registration with the CT scan images. FIG. 2 illustrates selection of a CT scan image as a part of a manual image registration process. As shown in FIG. 2, a series of CT scans are shown in a bottom row. A physician may select one of these images. As shown in FIG. 3, once one of the CT scan images is selected, a physician may select a corresponding ultrasound image. The physician may scroll through various images to select the corresponding ultrasound image. This process may be repeated multiple times.

Figure 4:
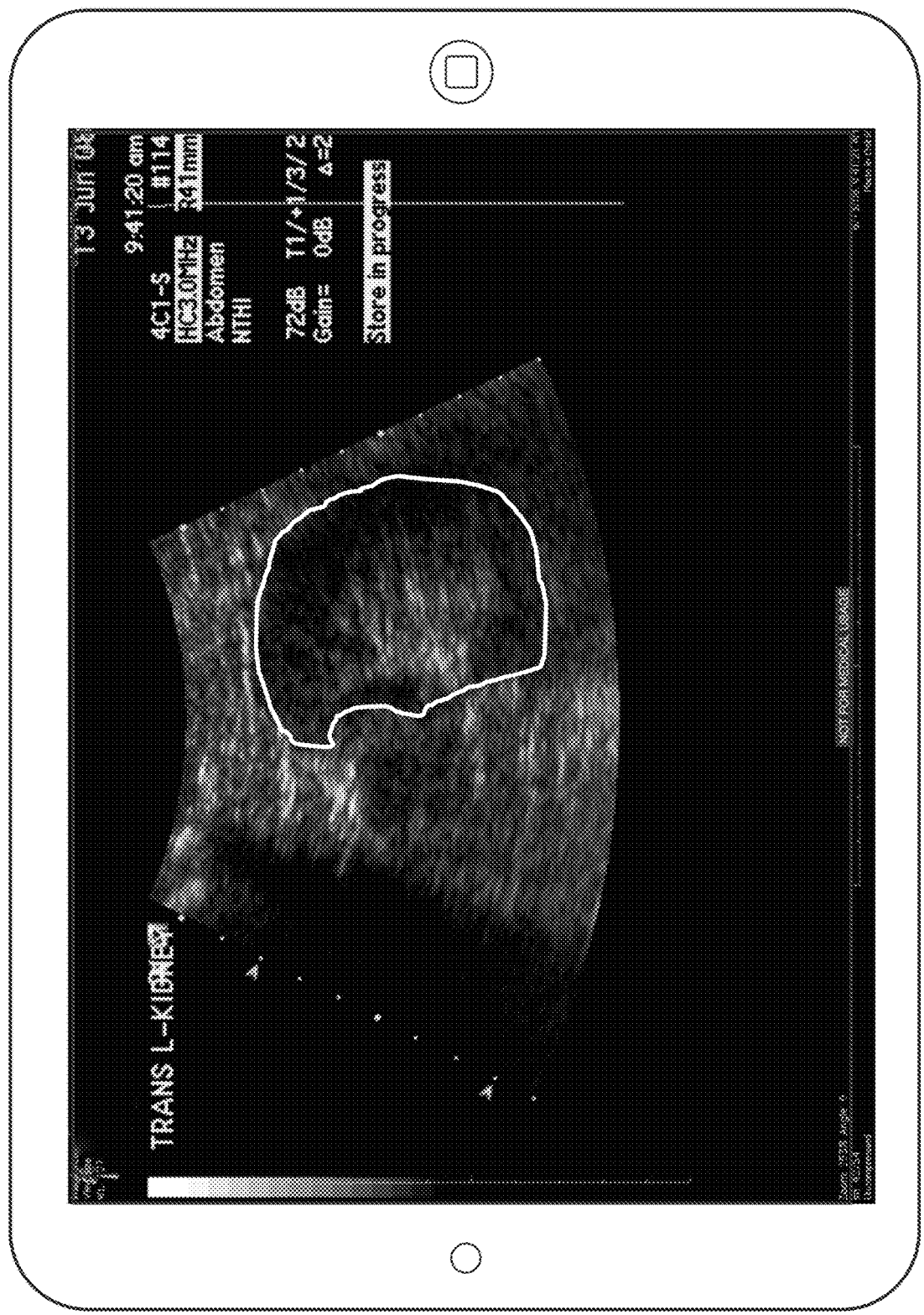
FIG. 4 illustrates manually outlining a kidney.

FIG. 4 illustrates an example of another step in a manual image registration process. As shown in FIG. 4, a physician may trace the contour or boundaries of an organ, in this instance, a kidney. Where a touchscreen display is used, a physician may simply trace the contour on the screen with their finger, although it is contemplated that digitizing tablets, mice, trackballs, joysticks, or other types of input devices may be used instead. Alternatively, instead of having an operator draw the complete contour, the operator may select points instead associated with the organ and these points may be used to identify the organ and/or to draw the contour.

Figure 5:
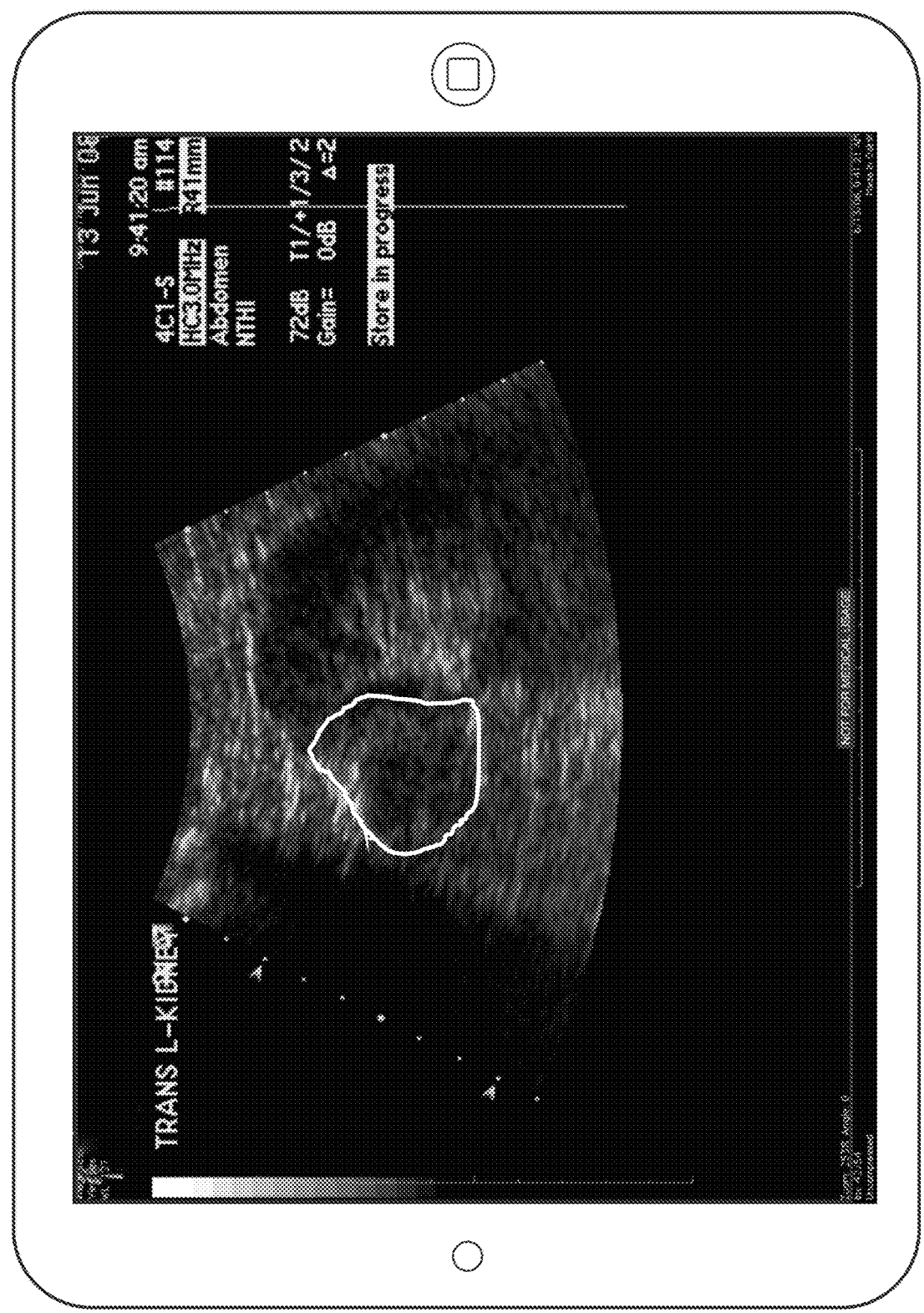
FIG. 5 illustrates manually outlining a lesion on the kidney.

FIG. 5 illustrates an example of another step in the manual image registration process. As shown in FIG. 5, a physician may trace the contour of a region of interest (such as a tumor or lesion) in a manner similar to tracing the organ. Similarly, the operator may select points associated with the region of interested (such as a targeted tumor or lesion).

Figure 6:
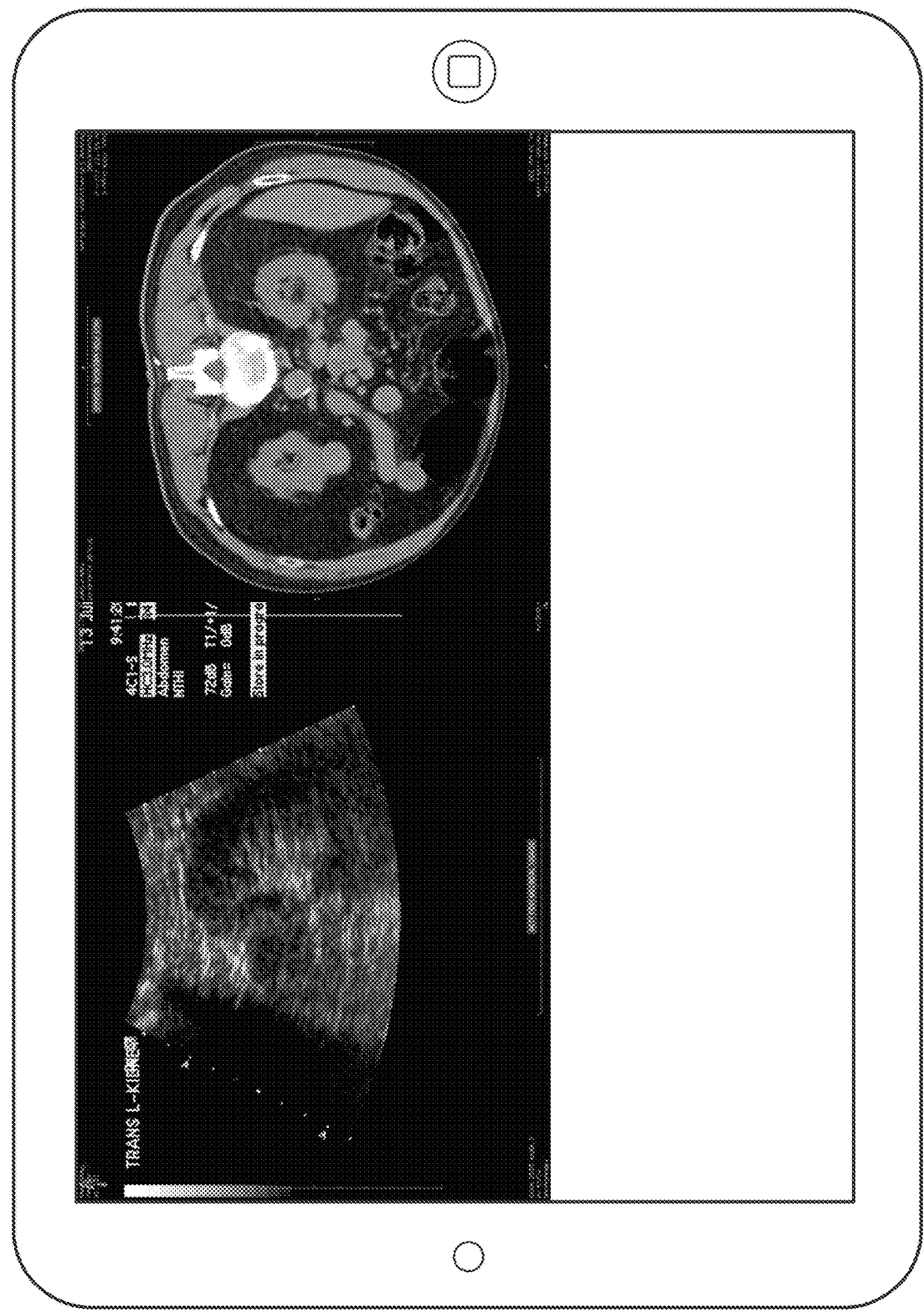
FIG. 6 illustrates a real-time display of ultrasound imagery and corresponding CT scan imagery.

FIG. 6 illustrates a real-time display of ultrasound imagery and corresponding CT scan imagery. As shown in FIG. 6 real-time renal ultrasound imagery is shown which is registered to renal CT scan images. In real-time as the ultrasound imagery is updated the corresponding CT image may be updated accordingly so that the operator is always viewing the most relevant CT scan. A number of different algorithms may be used for this process. These include merely identifying which of the ultrasound images used for registration is closest to the currently displayed ultrasound image and then displaying the CT scan which corresponds to the ultrasound images used for registration. Feature extraction of the organ or the region of interest may be performed to assist in this process. However, due to the manual registration process, the process is simplified relative to some type of process that attempts to perform automatic image registration.

Figure 7:
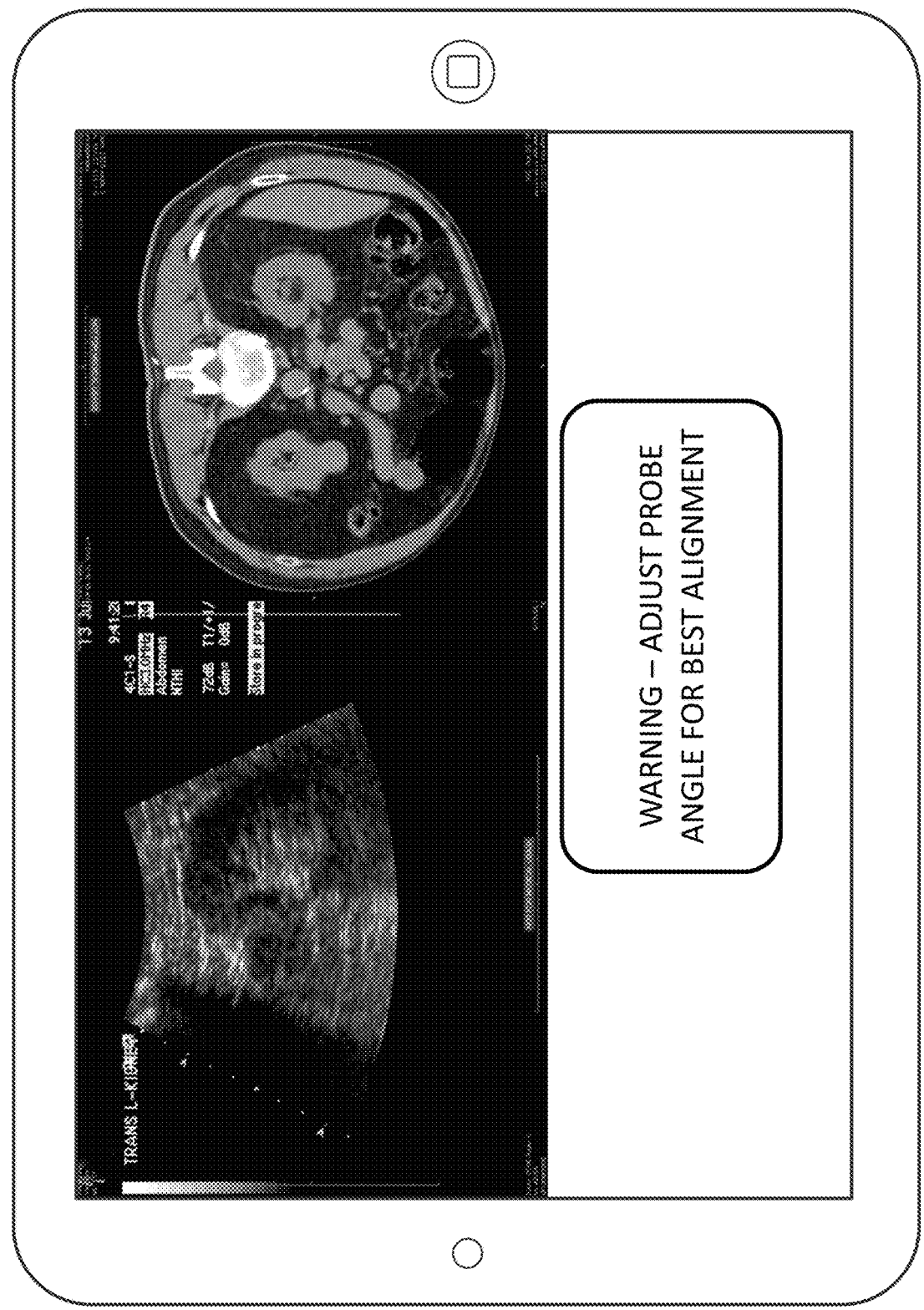
FIG. 7 illustrates an alert which may be provided during operation to indicate that the probe angle should be adjusted for best alignment.

Due to the manual image registration process the angle of the ultrasound probe should remain consistent in order to obtain the best alignment. FIG. 7 illustrates an alert which may be provided during operation to indicate that the probe angle should be adjusted for best alignment. The alert may be provided various ways including visually and our audibly.

Figure 8:
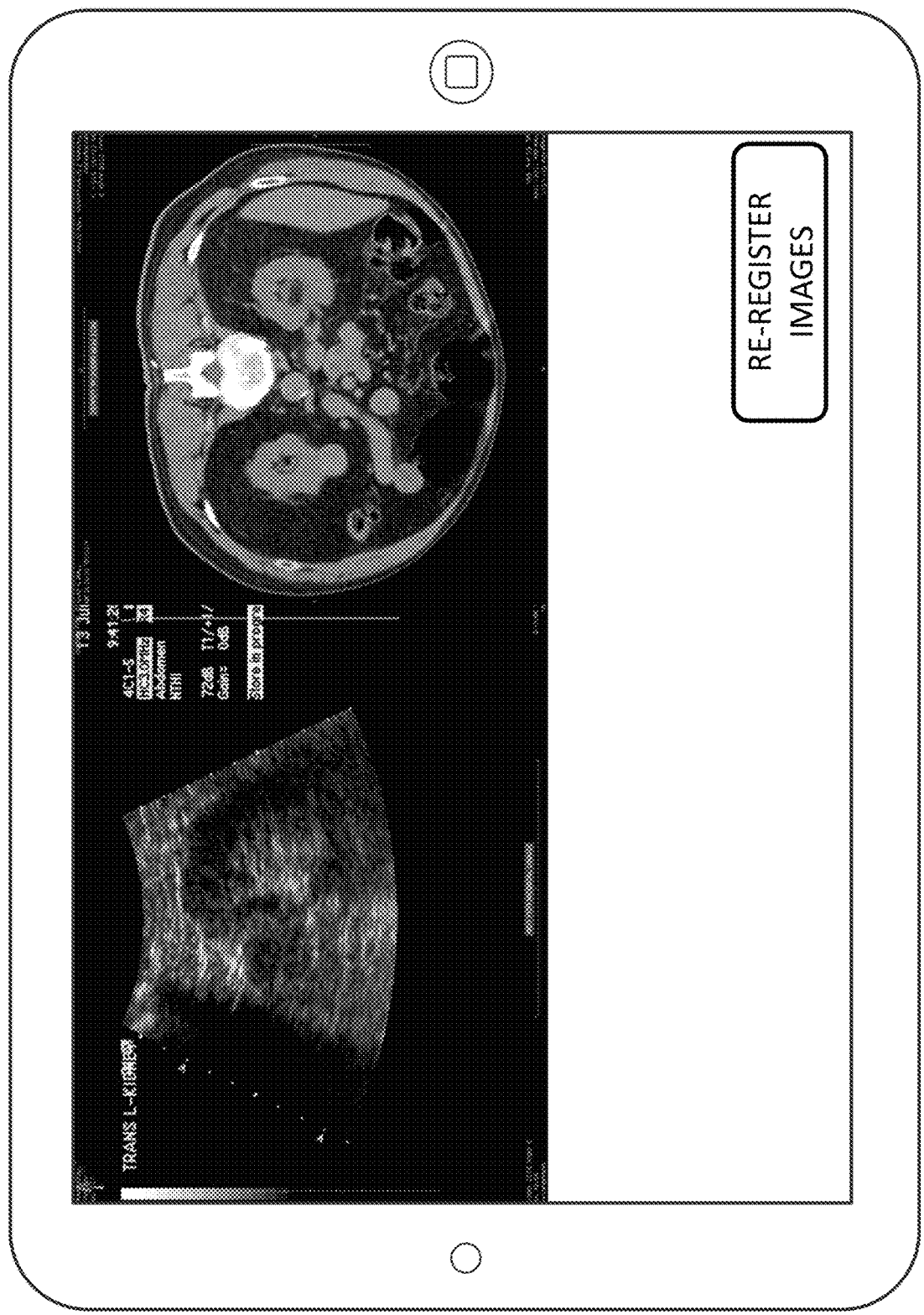
FIG. 8 illustrates that the user interface may provide for allowing a physician to re-register images at any time.

FIG. 8 illustrates that the user interface may provide for allowing a physician to re-register images at any time. If the software application has difficulty recognizing the ultrasound image (due to suboptimal image quality for example) which corresponds to the CT image or if the ultrasound operator becomes disoriented either to the position of the ultrasound probe on the patient's body or the angle of the probe, the operator may scroll through the CT scan images quickly to locate the desired CT image slice to reorient himself. This will then bring up the contour image of the initial ultrasound image used for registration and the region of interest (ROI)/targeted lesion. The operator may then adjust angle and position of the ultrasound to probe to match the landmarks marked at the beginning of the session. So during the actual procedure the ultrasound will be live and the CT images can be scrolled to change the contour/target.

Figure 9:
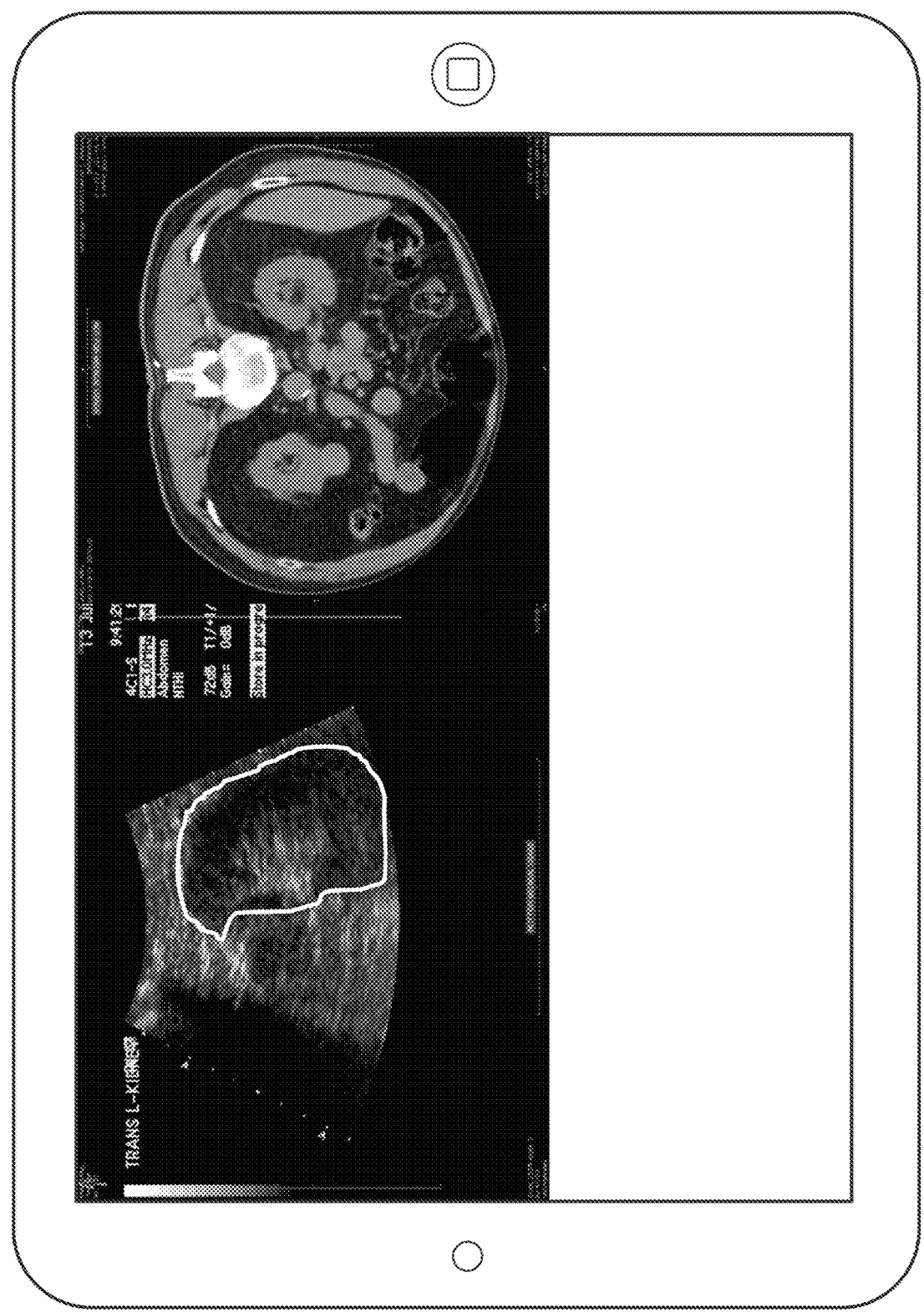
FIG. 9 illustrates another example of a real-time display in which the contour of the kidney is shown.

FIG. 9 illustrates another example of a real-time display in which the contour of the kidney is shown. It is contemplated that it in some instances it may be helpful to overlay the contour of the organ or region of interest over the ultrasound imagery.

Figure 10:
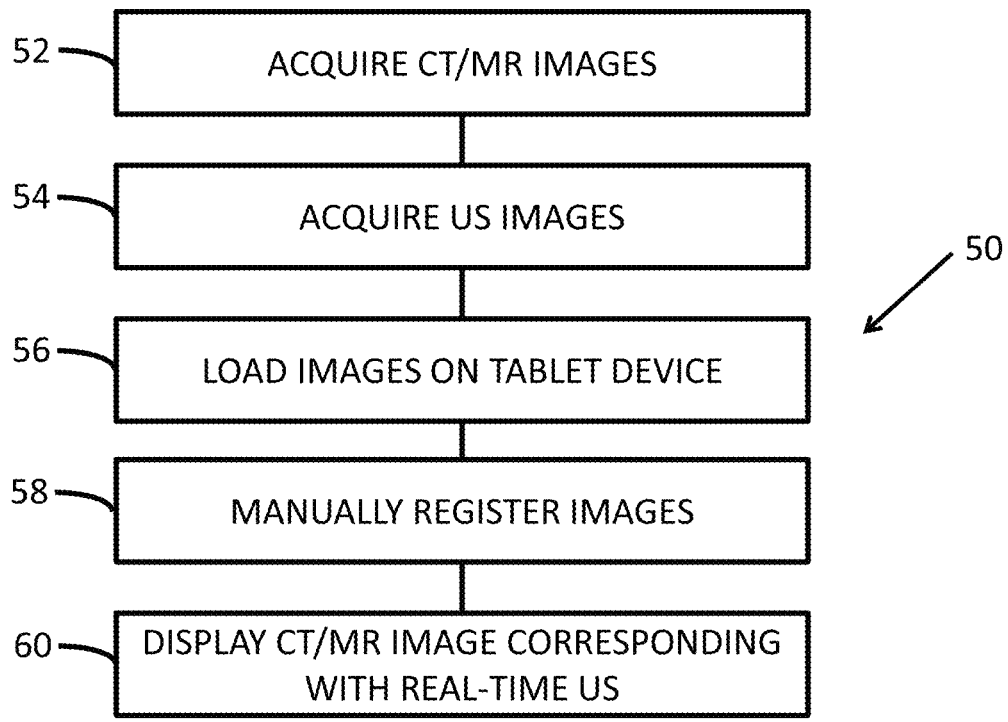
FIG. 10 illustrates a flow diagram of one example of a methodology for ultrasound and MR or CT fusion.

FIG. 10 illustrates a flow diagram of one example of a methodology for ultrasound and MR or CT fusion. A process 50 is shown. In step 52, CT or MR images are obtained. In step 54, ultra sound images are obtained. In step 56 the images are loaded onto a tablet device. In step 58 a manual image registration process is used. Then in step 60 a CT scan image or MR image corresponding with real-time ultrasound imagery is displayed.

In addition to using images associated with CT or MR, it is also contemplated that three-dimensional (3D) models may also be used. 3D models may be created from DICOM images or other types of images or image data. Where 3D models are used, a 3D model may be displayed to the user and the user may select a cross-section of the 3D model to be used for registration processes. During operation, if an alignment issue is determined either manually by the user or automatically by the software the user may be given an opportunity to either adjust their probe or else choose a different cross-section of the 3D model to align with the ultrasound imagery.

Figure 11:
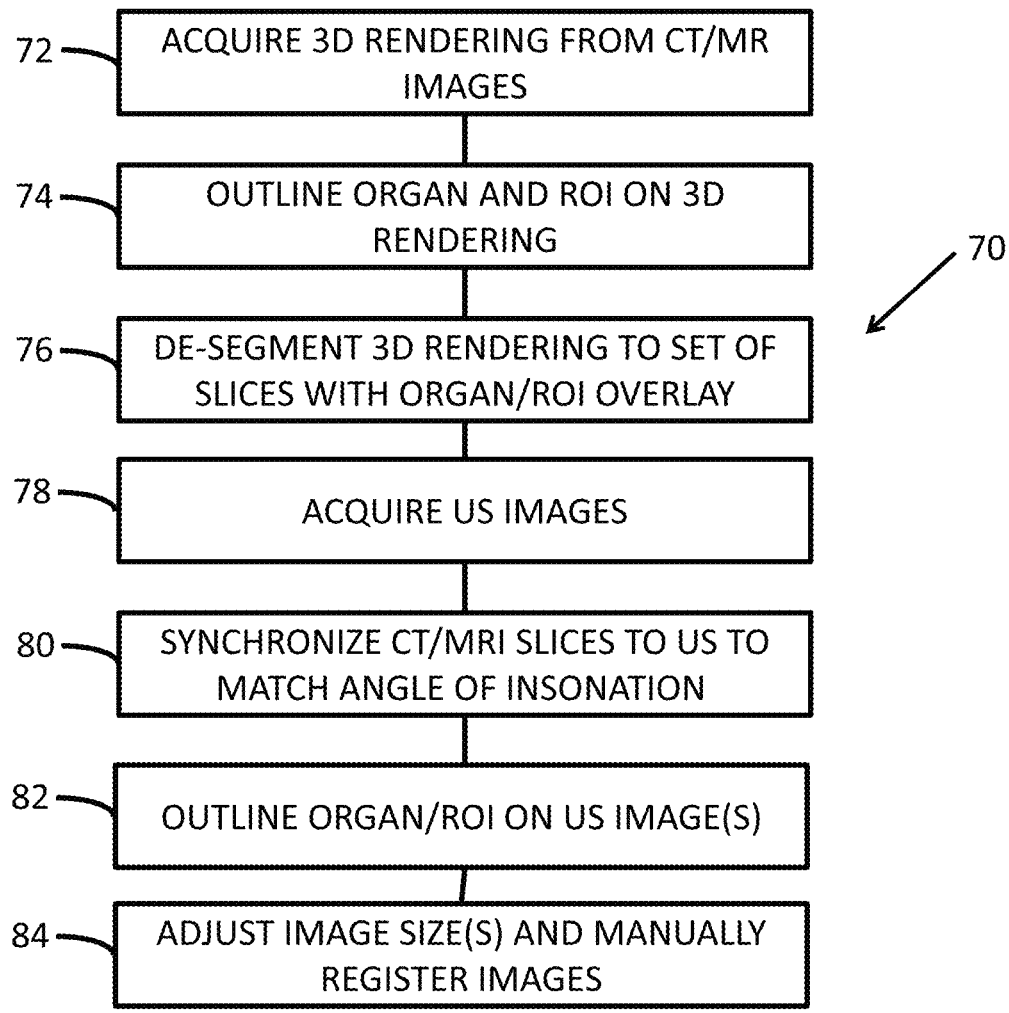
FIG. 11 illustrates a flow diagram of another example of a methodology for ultrasound and MR or CT fusion.

FIG. 11 illustrates another example of a method which may be used. In the method of FIG. 11, 3D models are used. In step 72, a 3D model or 3D rendering is obtained. The 3D model may be based on CT images or MR images or other acquired imagery. A 3D modeling or rendering program such as is known in the art may be used to generate the 3D model or rendering. In step 74 a physician may outline the organ and the region of interest on the 3D rendering. For example, the organ may be a kidney and the region of interest may be a lesion to be biopsied or treated. Note that the physician may be given control of the 3D rendering to rotate, resize, or provide other functionality. In step 76, the 3D rendering is de-segmented or otherwise processed to provide a set of slices but maintaining the outline or tracing made by the physician. Although the size of the set of slices may vary, 30 or 40 slices provides a reasonable number. This outline or tracing may form an overlay which overlays the various images. Next in step 78 the ultrasound images are acquired. In step 80, the CT/MRI slices may be synchronized with the ultrasound. Note that the angle of insonation may be matched as a part of the synchronization process. In step 82, the physician may outline the organ and region of interest on the ultrasound images. In step 84, the physician may adjust image sizes(s) and manually register the ultrasound images to the CT or MR images.

Once the images are registered, it is contemplated that where a tablet device is used, it may be placed in a sterile bag such as is already commercially available. At this point, the live ultrasound may be performed to locate the mass for biopsy or treatment. Once the optimal view for needle placement had been obtained, the operator may swipe the screen of the tablet device to select the appropriate overlay which best matches the live image. The operator may then hit a "toggle" button (either a soft button or physical button) on the tablet and bring up the corresponding CT or MR image. Scrolling up frame by frame through the CT or MR images may be performed by adjusting the ultrasound probe slightly to move it cepahald or caudad (toward the head or feet) on the patient's skin and pushing a "button" (which may be a soft button or physical button) to advance step by step (level by level) through the previously acquired ultrasound overlays and hitting a button to confirm the correct overlay. The corresponding CT or MR image may then be brought up on the tablet screen. A virtual needle may then be brought up on the CT or MR image which is adjustable by the operator to obtain the appropriate angle and depth. The needle trajectory visual guide or "raster" (such as a dotted line) may be selected to be displayed on the ultrasound overlay. The operator may then toggle between the CT or MR image and the ultrasound image with the raster or a split screen. Optimally, the raster may be exported to the ultrasound machine as well and displayed on the ultrasound machine viewing screen, that way the operator would have a larger image of the CT or MR image on the tablet and the large ultrasound machine viewing screen to visualize all structures clearly.

Although various examples are described herein, it is to be understood that the present invention contemplates numerous options, variations, and alternatives. For example, detailed examples have been provided where the organ is a kidney and the region of interest contains a lesion. It is to be understood that this is merely one application. The kidney has a relatively simple shape structure with soft tissue tumors which can be biopsied or ablated (such as through thermal ablation). However, the system may be used for other organs. For example, in general surgery application, the present invention may be used in the biopsy and ablation of liver tumors, the biopsy and ablation of retroperitoneal tumors, the drainage of abdominal and retro peritoneal abscess, the drainage of biliary obstruction, the biopsy, needle localization, and cryoablation of breast cancer. Other examples where the present invention may be used include in gynecology such as in the drainage of pelvic abscess and ovarian cysts. In addition, it is to be understood that various types of imagery may be used including CT imagery and MR imagery. It is to be further understood that 3D models may be generated from the CT imagery or the MR imagery and the 3D models may be used such that the ultrasound imagery is registered with the 3D model data. It is further to be understood that variations in the placement and relative placement of images being registered is contemplated. For example ultrasound images may be positioned above the MR/CT images or below the MR/CT images and the orientation of the images may be rotated based on the particular type of surgery being performed in order to provide the most convenient and intuitive view to the physician.

What is claimed is:

1. A method for fusion of live ultrasound imagery with computed tomography (CT) scan images or magnetic resonance images of an internal patient abdomen or a pelvis location of a patient by a healthcare practitioner, the method comprising steps of:

prior to a patient procedure being performed, at a point-of-care, on the patient by the healthcare practitioner, acquiring a first series of individual CT scan images or magnetic resonance images of the internal patient abdomen or pelvis location in a digital format that is capable of being digitally displayed;

prior to or during the patient procedure, acquiring a second series of individual ultrasound images of the internal patient abdomen or the pelvis location in said digital format;

after acquiring the first series and the second series, applying a healthcare-practitioner-controlled registration process on a digital computing device with a user interface to register N number of individual CT scan images or magnetic resonance images of the acquired first series with N number of individual ultrasound images of the acquired second series respectively, wherein N is a certain number, wherein the healthcare-practitioner-controlled registration process comprises:

displaying to the healthcare practitioner at the point-of-care on at least one registration digital display at least some individual CT scan images or magnetic resonance images of the acquired first series, concurrently displaying on the at least one registration digital display at least some individual ultrasound images of the acquired second series, and receiving N number of healthcare-practitioner-controlled registration selections, from the healthcare practitioner via the user interface, wherein the N number of registration selections comprise: selecting N number of individual ultrasound images from the displayed at least some individual ultrasound images and selecting N number of individual CT scan images or magnetic resonance images from the displayed at least some individual CT scan images or magnetic resonance images respectively corresponding thereto, for each respective healthcare-practitioner-controlled registration selection of said N number of healthcare-practitioner-controlled registration selections, generating and storing for retrieval from the digital computing device a respective registration linking a respective individual ultrasound image of the selected N number of individual ultrasound images with a respective individual CT scan image or magnetic resonance image of the selected N number of individual CT scan images or magnetic resonance images based on the respective healthcare practitioner registration selection; and during the patient procedure at the point-of-care, performing the following:
(a) acquiring and displaying on at least one point-of-care digital display associated with the digital computing device a live, real-time ultrasound imagery of the internal patient abdomen or the pelvis location of the patient,
(b) analyzing, by the digital computing device, the live, real-time ultrasound imagery, and identifying, by the digital computing device, an ultrasound image, from the registered N number of individual ultrasound images, that corresponds to the displayed live, real-time ultrasound imagery,
(c) identifying, by the digital computing device, a CT scan image or magnetic resonance image, from the registered N number of individual CT scan images or magnetic resonance images, that is registered to the identified ultrasound image by the respective registration link therebetween, and
(d) retrieving and concurrently displaying on the at least one point-of-care digital display the identified CT scan image or magnetic resonance image.

2. The method of claim 1 wherein the healthcare-practitioner-controlled registration process further comprises receiving from the healthcare practitioner a tracing of contours of or points related to an organ within said at least some individual ultrasound images and said at least one individual CT scan images or magnetic resonance images displayed on the at least one registration digital display.

3. The method of claim 2 wherein the tracing is received from the health care practitioner via an input device.

4. The method of claim 3 wherein the input device comprises a touch screen with drawing capabilities, a mouse, a trackball, or a joystick.

5. The method of claim 1 wherein the healthcare-practitioner-controlled registration process further comprises receiving from the healthcare practitioner a tracing of contours of or points related to a region of interest within said at least some individual ultrasound images and said at least one individual CT scan images or magnetic resonance images displayed on the at least one registration digital display.

6. The method of claim 1 wherein the first series and the second series are series of renal images respectively.

7. The method of claim 1 wherein the patient procedure comprises performance of a medical procedure.

8. The method of claim 7 wherein the medical procedure comprises a biopsy.

9. The method of claim 7 wherein the medical procedure comprises an ablation.

10. The method of claim 1 wherein the digital computing device is a tablet device.

11. The method of claim 1 wherein the step of acquiring the first series comprises obtaining the first series from a non-transitory computer readable storage media.

12. The method of claim 1 wherein the first series is in a DICOM format.

13. The method of claim 1 further comprising generating a three dimensional model associated with the first series.

14. The method of claim 13 further comprising:
presenting the three dimensional model to the healthcare practitioner on the at least one point-of-care digital display and;

receiving a selection of a cross-section of the three dimensional model from the healthcare practitioner, wherein the cross-section is associated with the first series.

15. The method of claim 1 wherein step (b) comprises comparing the displayed live, real-time ultrasound imagery to the registered individual digital ultrasound images via image recognition software executed on the digital computing device.

16. The method of claim 15 wherein the image recognition software comprises a feature recognition algorithm, and wherein said step of identifying the ultrasound image that corresponds to the displayed live, real-time ultrasound imagery is performed by executing said feature recognition algorithm on the digital computing device.

17. The method of claim 1 further comprising performing a healthcare-practitioner-controlled adjustment on the at least one registration display, wherein the healthcare-practitioner-controlled adjustment comprises adjusting positions of the selected N number of individual ultrasound images relative the selected N number of individual CT scan images or magnetic resonance images.

18. The method of claim 17 wherein said adjusting positions comprises:
displaying the selected N number of individual ultrasound images serially aligned in a first row,
displaying the selected N number of individual CT scan images or magnetic resonance images serially aligned in a second row, and
adjusting said positions via scrolling the first row relative to the second row or scrolling the second row relative to the first row.

19. The method of claim 1 further comprising modifying a respective healthcare-practitioner-controlled registration selection of the N number of healthcare-practitioner-controlled registration selections to re-register a respective individual CT scan image or magnetic resonance image of the selected N number of individual CT scan images or magnetic resonance images and a respective individual ultrasound image of the selected N number of individual ultrasound images.

20. The method of claim 1 further comprising updating the identified CT scan image or magnetic resonance image that is retrieved and concurrently displayed in response to a change in the acquired live, real time ultrasound imagery by repeating steps (b)-(d) in response to and in accordance with said change.

21. The method of claim 1 wherein step (b) comprises monitoring an angle of insonication for the acquired live, real-time ultrasound imagery and comparing the monitored angle of insonication to an angle of insonication of each of the registered N number of individual ultrasound images.

22. The method of claim 1 wherein the patient procedure comprises penetrating the patient with a needle or probe, the method further comprising generating and displaying on the at least one point-of-care digital display a simulated needle or probe having a position on the at least one point-of-care digital display that is indicative of a placement of the needle or probe relative to the patient.

23. A method for fusion of live ultrasound imagery with computed tomography (CT) scan images or magnetic resonance (MR) images for use on a computing device having a digital display, the method comprising steps of:
downloading into the computing device a first series of individual digital CT scan images or MR images related to an internal abdomen or pelvic structure of a patient;

downloading into the computing device a second series of individual digital ultrasound images related to the internal abdomen or pelvic structure of the patient;

displaying on the digital display of the computing device a registration graphical user interface to a user for applying a user-controlled registration process on the computing device to register one or more individual digital CT scan images or MR images of the first series with one or more individual digital ultrasound images of the second series respectively, wherein the user-controlled registration process comprises:

displaying to the user on the digital display said one or more individual digital CT scan images or MR images, concurrently displaying said one or more individual digital ultrasound images to the user on the digital display, receiving one or more user input selections from the user, via the registration graphical user interface or other user control device, wherein the one or more input selections comprise: selecting one or more individual digital ultrasound images from the displayed one or more individual digital ultrasound images and selecting one or more individual digital CT scan images or MR images from the displayed one or more individual digital CT scan images or MR images respectively corresponding thereto, and for each respective selection of the one more input selections, generating a respective storable registration linking a respective individual digital CT scan image or magnetic resonance image of the selected one or more individual digital CT scan images or MR images with a respective individual digital ultrasound image of the selected one or more individual digital ultrasound images;

receiving into the computing device live, real-time ultrasound imagery of the internal abdomen or pelvis structure of the patient from an ultrasound system;

displaying on the digital display of the computing device a live graphical user interface comprising the live, real-time ultrasound imagery and a matching CT scan image or MR image by performing the following with the computing device:

(a) identifying, from the registered one or more individual digital ultrasound images, an individual digital ultrasound image that correlates to the currently displayed live, real-time ultrasound imagery and (b) identifying, from the registered one or more individual digital CT scan images or MR images, an individual digital CT scan image or MR image that is registered to the identified individual digital ultrasound image the respective storable registration link therebetween, and (c) displaying, on the live graphical user interface, the identified individual digital CT scan image or MR image as the matching CT scan image of MR image.

24. The method of claim 23, wherein at least one step selected from the group consisting of said selecting one or more individual ultrasound image and said selecting one or more individual digital CT scan images or MR images comprises receiving a respective selection thereof via the registration graphical user interface.

25. The method of claim 24 further comprising, receiving, from the user via the registration graphical user interface, a tracing of or points related to a contour of an organ or region of interest of the patient.

26. The method of claim 23 further comprising downloading into the computing device a three dimensional model associated with the first series.

27. The method of claim 23 wherein the computing device is a tablet device with a touchscreen display.

28. The method of claim 23 wherein step (c) is performed during performance of a medical procedure.

29. The method of claim 28 wherein the medical procedure is a biopsy or an ablation.

* * * * *